US012778552B2

(12) United States Patent
Zhang et al.

(10) Patent No.: US 12,778,552 B2
(45) Date of Patent: Nov. 3, 2026

(54) ULTRASOUND SCANNER WITH AN IMPACT-RESISTANCE SYSTEM

(71) Applicant: FUJIFILM SonoSite, Inc., Bothell, WA (US)

(72) Inventors: Jimin Zhang, Bellevue, WA (US); Edward Tea, Bellevue, WA (US); Bin-Da Chan, Bothell, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 851 days.

(21) Appl. No.: 18/306,794

(22) Filed: Apr. 25, 2023

(65) Prior Publication Data

US 2024/0358352 A1 Oct. 31, 2024

(51) Int. Cl.
*A61B 8/00* (2006.01)

(52) U.S. Cl.
CPC .......... *A61B 8/4483* (2013.01); *A61B 8/4272* (2013.01)

(58) Field of Classification Search
CPC ................ A61B 8/4444; A61B 8/4483; A61B 8/4272; A61B 8/4427
See application file for complete search history.

(56) References Cited

U.S. PATENT DOCUMENTS

2005/0165313 A1* 7/2005 Byron .................... G10K 11/02 600/459
2014/0211587 A1* 7/2014 Kiyose ................ G01S 7/52053 367/87

* cited by examiner

*Primary Examiner* — J. San Martin
(74) *Attorney, Agent, or Firm* — Colby Nipper PLLC

(57) ABSTRACT

Systems and methods for an ultrasound scanner with an impact-resistance system are described. In some implementations, the impact-resistance system reduces acceleration components associated with an impact force applied to an enclosure of the ultrasound scanner or directly to an acoustic lens of a transducer array of the ultrasound scanner. The impact-resistance system distributes the acceleration components from the transducer array to the enclosure via couplings with soft and elastic materials. Some of the couplings may be located between the enclosure and elongated members embedded in backing material of the transducer array. Some of the couplings may be located between the enclosure and a flange that extends from the acoustic lens into a channel in the enclosure. Implementing the impact-resistance system described herein improves reliability of the transducer array without sacrificing performance or usability, particularly for ultraportable scanners.

14 Claims, 10 Drawing Sheets

Section A–A

300

400

500

600

700

Section A–A

900

1000

ULTRASOUND SCANNER WITH AN IMPACT-RESISTANCE SYSTEM

BACKGROUND

Ultrasound scanners (e.g., probes) are extremely sensitive devices that are generally handheld and used to scan a patient's anatomy. These ultrasound scanners may be used, for example, in an office by clinicians, in an emergency room (ER) trauma bay by a doctor or nurse, on a battlefield by military personnel, in an ambulance by an emergency medical technician (EMT), and so on. Because ultrasound scanners are handheld, they can easily be dropped by an operator. When dropped, an ultrasound scanner is at significant risk of damage to its transducer elements, particularly if dropped directly on its lens. While some ultrasound scanners are connected to an ultrasound machine via a relatively short wire or cord that can slow the fall of a dropped ultrasound scanner and thereby reduce impact forces from a hard surface (e.g., floor, ground, table, etc.), other ultrasound scanners are wirelessly connected to the ultrasound machine and are therefore still at significant risk of damage to their transducer elements.

Previous solutions have added housing material around the lens (e.g., more metal, more plastic, etc.) of the ultrasound scanner to make it more robust. While such additional housing can reduce a peak acceleration resulting from an impact force, it also results in a heavier, larger, and often more rugged and expensive scanner that sacrifices usability and performance (e.g., sensitivity). Further, the weight of such a heavier and larger ultrasound scanner creates a moment of force (e.g., a measure of the force's tendency to cause a body to rotate about a specific point or axis) on the operator's hand, which can cause the operator to become fatigued.

One solution includes limiting the length of the wire or using a spiral cord. This solution, however, only applies to wired ultrasound scanners and can be problematic because the wire or cord can hinder mobility by getting caught on objects, getting in the way, and so forth.

Although various solutions have been implemented to protect the transducer elements from impact forces when the ultrasound scanner is dropped, conventional solutions have limitations that sacrifice performance (e.g., sensitivity), economy, and/or usability of the ultrasound scanner.

SUMMARY

Systems and methods for an ultrasound scanner with an impact-resistance system are disclosed. In some implementations, the impact-resistance system reduces acceleration components associated with an impact force applied to an enclosure of the ultrasound scanner or directly to an acoustic lens of a transducer array of the ultrasound scanner. The impact-resistance system distributes the acceleration components from the transducer array to the enclosure via couplings with soft and elastic materials. Some of the couplings can be located between the enclosure and elongated members embedded in backing material of the transducer array. Some of the couplings can be located between the enclosure and a flange that extends from the acoustic lens into a channel in the enclosure. The impact-resistance system can also include the acoustic lens being recessed relative to the enclosure so that a majority of an impact force from a flat surface is applied to the enclosure rather than directly to the acoustic lens. Implementing the impact-resistance system disclosed herein improves reliability of the transducer array without sacrificing performance or usability, particularly for ultraportable scanners.

In some aspects, an ultrasound scanner is disclosed. The ultrasound scanner includes an enclosure, a transducer assembly, and an impact-resistance system. The enclosure extends between the first end and the second end. The transducer assembly is disposed at the first end of the enclosure and coupled to system electronics of an ultrasound machine. The transducer assembly is configured to transmit ultrasound energy from one or more transducer elements toward a subject and receive ultrasound echoes from the subject for conversion by the one or more transducer elements into electrical signals usable by the system electronics to generate an ultrasound image. The transducer assembly includes a backing material disposed within the enclosure, a piezoelectric material disposed adjacent to the backing material, and an acoustic lens stacked with the piezoelectric material such that the piezoelectric material is between the acoustic lens and the backing material. The acoustic lens includes the following: an acoustic window configured to interface with the subject; a center axis that intersects the acoustic window, the piezoelectric material, and the backing material; and sidewalls connected to the acoustic window and extending inwardly toward an interior of the enclosure in a direction substantially parallel to the center axis of the acoustic lens. The impact-resistance system comprises a flange extending from the sidewalls of the acoustic lens in an outward direction away from the center axis of the acoustic lens and into a channel defined by the enclosure.

In some aspects, an ultrasound scanner is disclosed, which includes an enclosure, a transducer assembly, and an impact-resistance system. The enclosure extends along a central axis between a first end and a second end. The transducer assembly is disposed at the first end of the enclosure and communicatively coupled to system electronics of an ultrasound machine. Also, the transducer assembly is configured to transmit ultrasound energy from one or more transducer elements toward a subject and receive ultrasound echoes from the subject for conversion by the one or more transducer elements into electrical signals usable by the system electronics to generate an ultrasound image. The transducer assembly includes a backing material, a piezoelectric material, and an acoustic lens stacked with the piezoelectric material and the backing material along the central axis. The acoustic lens includes an acoustic window forming an outer surface of the acoustic lens. The transducer assembly also includes one or more elongated members embedded in the backing material and extending outwardly from opposing sides of the backing material and into a corresponding hole in the enclosure. The impact-resistance system comprises an elastic material disposed between the one or more elongated members and the enclosure to provide an interfacing bushing for attenuating an impact force applied to the enclosure or to the acoustic lens.

BRIEF DESCRIPTION OF THE DRAWINGS

The appended drawings illustrate examples and are, therefore, exemplary embodiments and not considered to be limiting in scope.

DETAILED DESCRIPTION

Conventional ultrasound scanners, particularly wireless scanners, are handheld and therefore at high risk of being dropped, which can result in considerable damage to transducer elements of the ultrasound scanner. Previous solutions have drawbacks that sacrifice usability and/or performance of the ultrasound scanner.

Accordingly, disclosed herein is an ultrasound scanner with an impact-resistance system, which increases device reliability by reducing a risk of damage to the transducer elements when the ultrasound scanner is dropped. The ultrasound scanner described herein includes various soft and elastic couplings and other structural features that help divert, distribute, and/or absorb acceleration components of impact forces applied to a lens side of the scanner, which reduces the amount of acceleration applied to piezoelectric elements of a transducer array of the ultrasound scanner.

Ultrasound System

Figure 1:
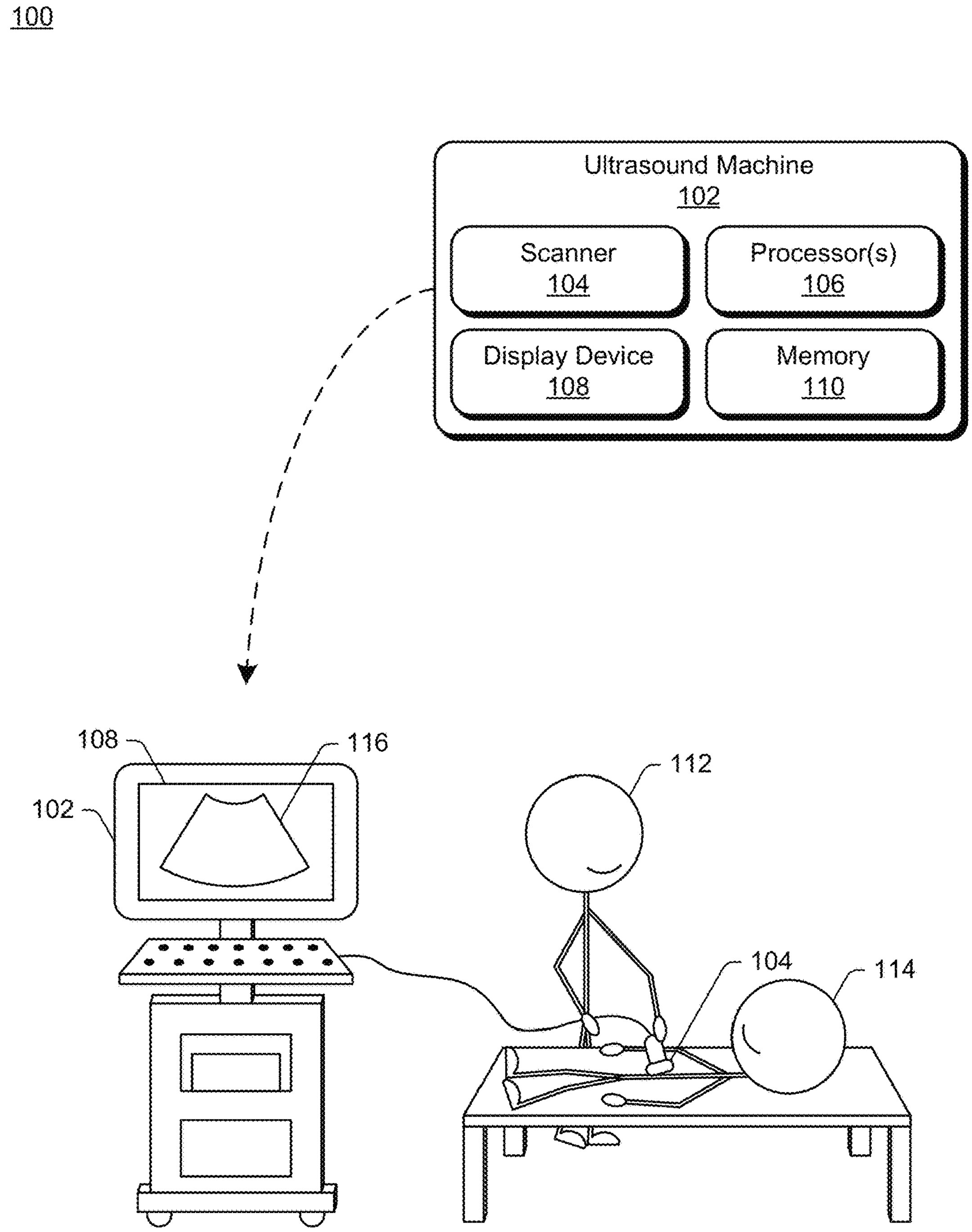
FIG. 1 illustrates an example environment for an ultrasound system having an ultrasound scanner, in accordance with one or more implementations.

FIG. 1 illustrates an example environment for an ultrasound system 100 having an ultrasound scanner, in accordance with one or more implementations. Generally, the ultrasound system 100 includes an ultrasound machine 102, which generates data based on high-frequency sound waves reflecting off body structures. The ultrasound machine 102 includes various components, some of which include a scanner 104, one or more processors 106, a display device 108, and a memory 110.

A user 112 (e.g., nurse, ultrasound technician, operator, sonographer, etc.) directs the scanner 104 toward a patient 114 to non-invasively scan internal bodily structures (e.g., organs, tissues, etc.) of the patient 114 for testing, diagnostic, or therapeutic reasons. In some implementations, the scanner 104 includes an ultrasound transducer array and electronics communicatively coupled to the ultrasound transducer array to transmit ultrasound signals to the patient's anatomy and receive ultrasound signals reflected from the patient's anatomy. In some implementations, the scanner 104 is an ultrasound scanner, which can also be referred to as an ultrasound probe.

The display device 108 is coupled to the processor 106, which processes the reflected ultrasound signals to generate ultrasound data. The display device 108 is configured to generate and display an ultrasound image (e.g., ultrasound image 116) of the anatomy based on the ultrasound data generated by the processor 106 from the reflected ultrasound signals detected by the scanner 104. In some aspects, the ultrasound data includes the ultrasound image 116 or data representing the ultrasound image 116.

Figure 2:
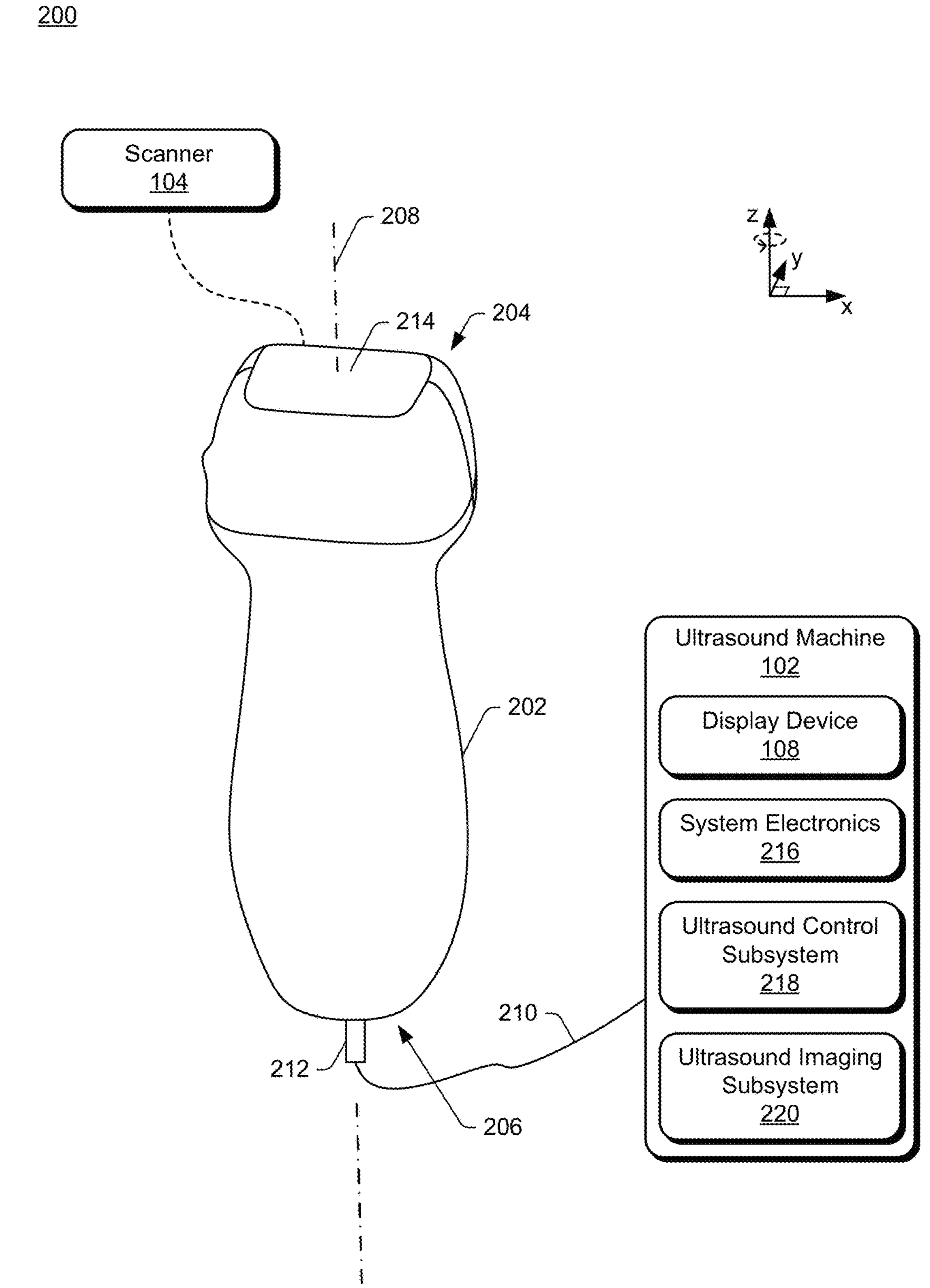
FIG. 2 illustrates an example implementation of the ultrasound scanner from FIG. 1.

FIG. 2 illustrates an example implementation 200 of the ultrasound scanner 104 from FIG. 1. The scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The scanner 104 is electrically coupled to an ultrasound imaging system (e.g., the ultrasound machine 102) via a cable 210 that is attached to the proximal end portion 206 of the scanner 104 by a strain relieve element 212. In some implementations, the scanner 104 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth.

In some implementations, the system electronics 216 include one or more processors (e.g., the processor(s) 106 from FIG. 1), integrated circuits, application-specific integrated circuits (ASICs), Field Programmable Gate Arrays (FPGAs), amplifiers, filters, and power sources to support functioning of the ultrasound machine 102. In some implementations, the ultrasound machine 102 also includes an ultrasound control subsystem 218 having one or more processors. At least one processor, FPGA, or ASIC causes electrical signals to be transmitted to the transducer(s) of the scanner 104 to emit sound waves and also receives electrical pulses from the scanner 104 that were created from the returning echoes. One or more processors, FPGAs, or ASICs process the raw data associated with the received electrical pulses and form an image that is sent to an ultrasound imaging subsystem 220, which causes the image (e.g., the image 116 in FIG. 1) to be displayed via the display device 108. Thus, the display device 108 displays ultrasound images from the ultrasound data processed by the processor(s) of the ultrasound control subsystem 218. The ultrasound images can include sequences of images in a video clip. Additionally or alternatively, the ultrasound images can include three-dimensional (3D) images.

In some implementations, the ultrasound machine 102 also includes one or more user input devices (e.g., a keyboard, a cursor control device, a microphone, a camera, etc.) that input data and enable taking measurements from the display device 108 of the ultrasound machine 102. The ultrasound machine 102 can also include a disk storage device (e.g., computer-readable storage medium such as read-only memory (ROM), a Flash memory, a dynamic random-access memory (DRAM), a NOR memory, a static random-access memory (SRAM), a NAND memory, and so on) for storing data from an ultrasound examination, including the acquired ultrasound images. In addition, the ultrasound machine 102 can include a printer that prints the image from the displayed data. To avoid obscuring the techniques described herein, such user input devices, disk storage device, and printer are not shown in FIG. 2.

Figure 3:
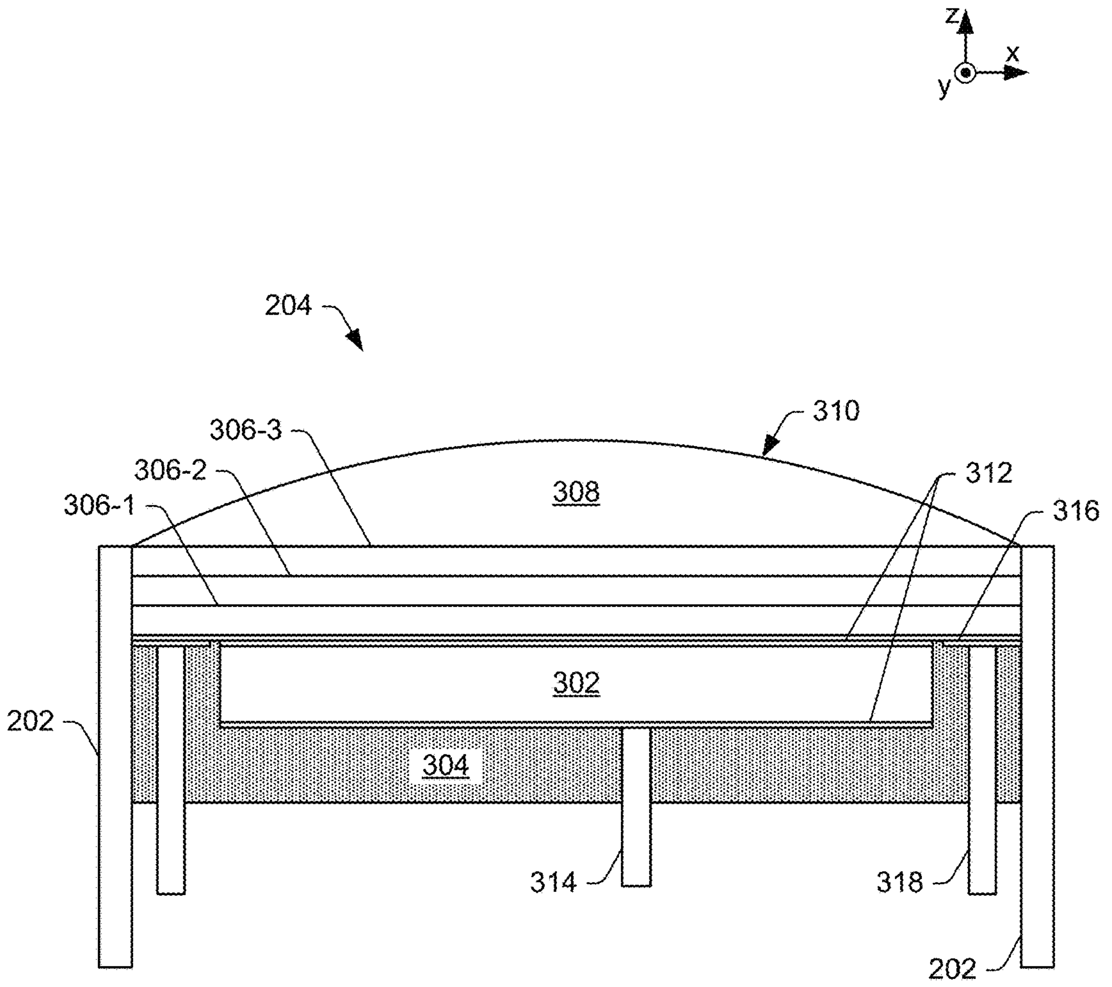
FIG. 3 illustrates a cross-section of an example array architecture and interconnection for a high-sensitivity transducer of an ultrasound scanner.

FIG. 3 illustrates a cross-section 300 of an example array architecture and interconnection for a high-sensitivity transducer of an ultrasound scanner. The cross-section 300 represents a cross-section of the distal end portion 204 of the ultrasound scanner 104 in FIG. 2.

In the illustrated example, the ultrasound scanner (e.g., the ultrasound scanner 104 of FIG. 2) includes transducer piezoelectric ceramic elements (e.g., piezoelectric material 302) sandwiched between a backing material 304 and a set of matching layers 306 (e.g., matching layers 306-1, 306-2, and 306-3). On the side of the set of matching layers 306 opposite from the piezoelectric material 302 is an acoustic lens (e.g., lens 308), which has an outer surface 310 facing outward (away from the proximal end portion 206 shown in FIG. 2). In the illustrated example, the outer surface 310 of the lens 308 is convex (e.g., curved toward the set of matching layers 306). In other examples, the outer surface 310 of the lens 308 can be substantially planar or concave (e.g., curved away from the set of matching layers 306).

The piezoelectric material 302 includes crystals with electrodes (e.g., electrodes 312) formed by, for example, plating a thin film of gold or silver on the crystal surface. The piezoelectric material 302 can be made of any suitable material, an example of which is lead zirconate titanate (PZT). The electrodes 312 can include a first electrode between the piezoelectric material 302 and the set of matching layers 306 and a second electrode between the piezoelectric material 302 and the backing material 304. In the illustrated example, the first electrode is adjacent to the front side of the piezoelectric material 302 (e.g., facing the lens 308) and the second electrode is adjacent to the backside of the piezoelectric material 302 (e.g., facing the backing material 304 and the proximal end of the scanner).

The set of matching layers 306 provides an acoustic impedance gradient for acoustic energy generated by the piezoelectric material 302 to smoothly penetrate the body tissue of the patient and for the reflected acoustic waves (the returning echo) to smoothly return to the piezoelectric material 302 for detection. In some implementations, the set of matching layers 306 includes a single matching layer. In other implementations, the set of matching layers 306 includes multiple matching layers in a stack.

In some implementations, the backing material 304 has a U-shaped cross-section having a recessed area for receiving the piezoelectric material 302. In this way, the backing material 304 provides structural support on the backside (away from the lens 308) as well as lateral sides (sides intersecting the x-axis and/or the y-axis) of the piezoelectric material 302. Accordingly, a portion of the backing material 304 is between the piezoelectric material 302 and the enclosure 202 (e.g., in the x- and y-directions). The backing material 304 can be made of various materials. Some examples include tungsten, iron, magnesium, and aluminum. In some implementations, the backing material 304 is a composite support material including, for example, an epoxy joined with tungsten particles. The backing material 304 is configured to prevent backward emitted sound waves from echoing and ringing back into the piezoelectric material 302 for detection.

The ultrasound scanner 104 also includes an electrical connection 314 to a power supply to provide current (e.g., alternating current) to the second electrode. In addition, a ground electrode 316 provides an electrical connection to ground 318 and serves as a terminal of the backside of the piezoelectric material 302.

Figure 4:
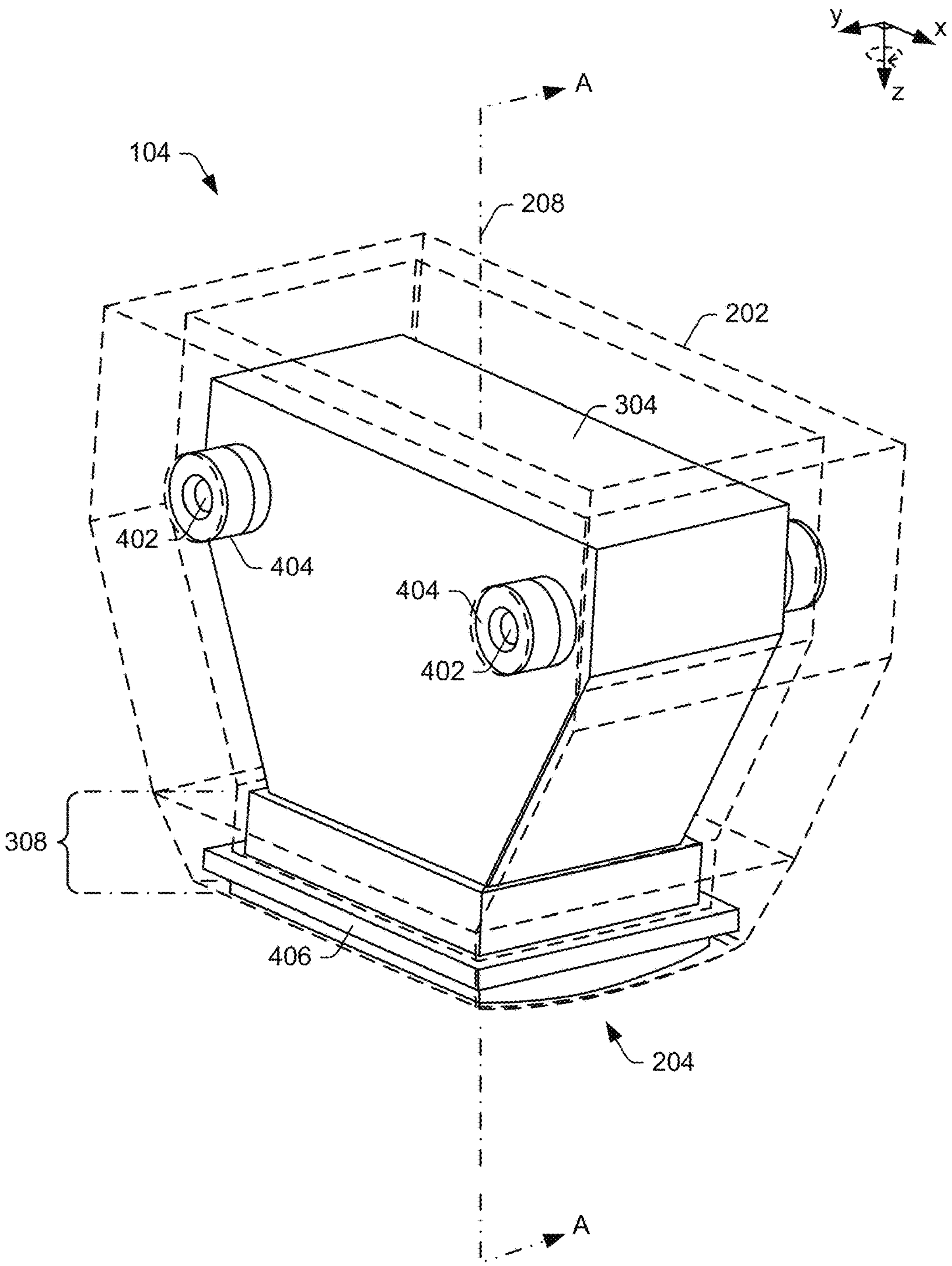
FIG. 4 illustrates a perspective view of a portion of an example ultrasound scanner with an impact-resistance system.

FIG. 4 illustrates a perspective view 400 of a portion of an example ultrasound scanner with an impact-resistance system. The impact-resistance system described herein is configured to mitigate acceleration forces transferred to the transducer array (and particularly to the piezoelectric material 302) due to an impact force applied to the ultrasound scanner 104, and particularly to the distal end portion 204 of the ultrasound scanner 104.

In FIG. 4, a portion of the ultrasound scanner 104 is shown that is proximate to the distal end portion 204 of the ultrasound scanner 104. In some implementations, one or more elongated members 402 (e.g., rods, dowels, pins, pegs, bars, tubes, screws, bolts, etc.) embedded in the backing material 304 are used to anchor the backing material 304 to the enclosure 202. For example, the elongated members 402 can pass through the backing material 304 and protrude from opposing sides of the backing material 304. In some implementations, the elongated members 402 extend in a direction that is orthogonal to the central axis 208 of the enclosure 202. In some implementations, each elongated member 402 is positioned such that a lengthwise dimension (e.g., longest dimension) of the elongated member 402 is substantially parallel to a plane defined by one of the matching layers 306 (shown in FIG. 3) or by the piezoelectric material 302 (shown in FIG. 3). In some implementations, each elongated member 402 is positioned such that the lengthwise dimension of the elongated member 402 is substantially orthogonal to the central axis 208 of the enclosure 202.

When assembled to the enclosure 202, each protruding end of the elongated member 402 extends into a corresponding hole (not shown) in the enclosure 202. To avoid a hard contact between the elongated member 402 and the enclosure 202, the impact-resistance system can include a backing-housing interface in the form of an elastic material 404 (e.g., elastic bushing, O-ring, silicon rubber, sealant, adhesive, etc.). The elastic material 404 is used as an interfacing bushing for attenuating impact energy applied to the enclosure 202. Further, the elastic material 404, which acts as a spring and a damper, provides a cushion between the elongated member 402 and the enclosure 202, and correspondingly between the enclosure 202 and the backing material 304. In this way, when the ultrasound scanner 104 is subjected to an impact force, the elastic material 404 absorbs a portion of the impact force without transferring that portion of the impact force to the backing material 304 and then to the piezoelectric material 302. Accordingly, the elastic material 404 is configured to reduce the amount of impact force transferred from the enclosure 202 to the piezoelectric material 302.

The impact-resistance system can also include a lens-housing interface in the form of a flange and a channel. For example, the lens 308 can include a flange 406 (e.g., a protruding or projecting ridge, lip, rim, collar, ring, etc. on an object) disposed on one or more lateral sides (e.g., sides intersecting the x-axis and/or the y-axis) of the lens 308 such that the flange 406 extends outwardly, away from the central axis 208. In some implementations, the flange 406 extends in a direction orthogonal to the central axis 208. In other implementations, the flange 406 extends in a direction that is non-parallel to the central axis 208, including a direction that is non-orthogonal to the central axis 208. The flange 406 extends into a corresponding channel (not shown in FIG. 4) in the enclosure 202. This flange-and-channel interaction is described in further detail with respect to FIG. 9.

The impact-resistance system can also include a recessed lens. For example, the lens 308 can be inset inwardly from an exterior surface of the enclosure 202 at the distal end portion 204 by a predefined distance. Further discussion of the recessed lens is included in relation to FIG. 9.

Figure 5:
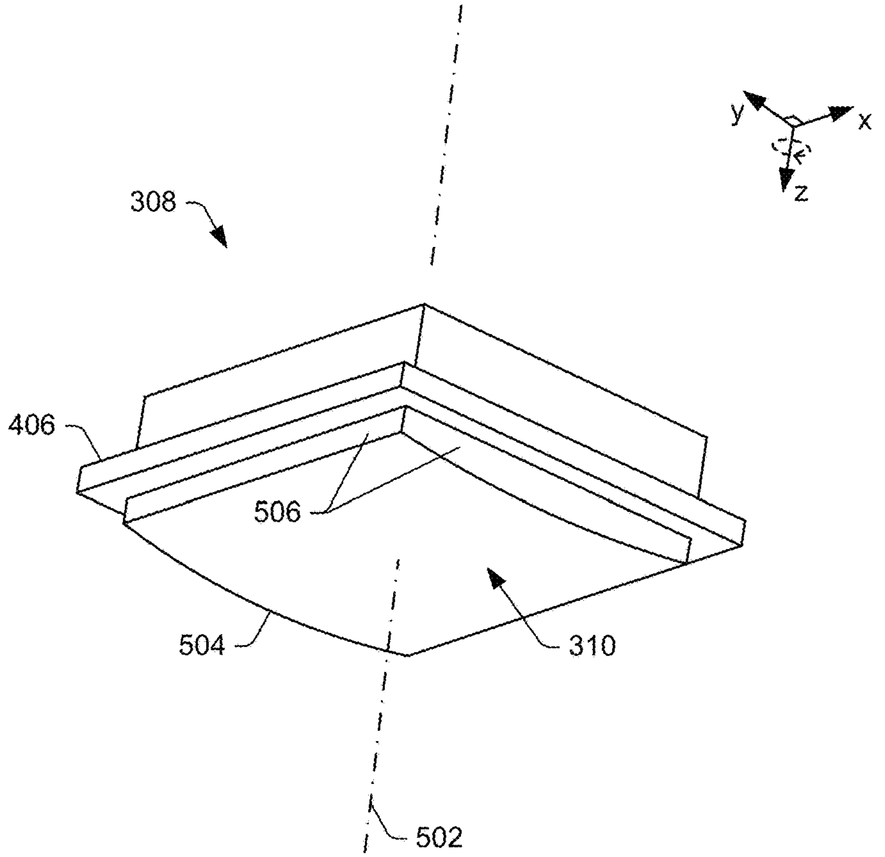
FIG. 5 illustrates an example implementation of a lens of the ultrasound scanner from FIG. 4.

FIG. 5 illustrates an example implementation 500 of an acoustic lens (e.g., the lens 308) of an ultrasound scanner (e.g., the ultrasound scanner 104 from FIG. 1). In the illustrated example, the lens 308 includes a center axis 502 passing through an acoustic window 504. The acoustic window 504 forms the outer surface 310 of the lens 308. When assembled, the center axis 502 of the lens 308 can be coaxial with the central axis 208 of the enclosure 202 shown in FIGS. 2 and 4. The outer surface 310 of the acoustic window 504 can be convex. Because the lens 308, in operation, is usually used with ultrasound gel, the material of the lens 308 may be non-toxic, durable, and chemically resistant to the ultrasound gel. Some example materials for the lens 308 include rubber, silicone (e.g., room-temperature-vulcanizing (RTV) silicone), plastic, and/or elastomer.

As illustrated and as mentioned above, the lens 308 includes the flange 406 extending outwardly away from the center axis 502. The flange 406 extends outwardly from one or more lateral sides of the lens 308. In aspects, the flange 406, the acoustic window 504, and other parts of the lens 308 form a single body for the lens 308. The lens 308 also includes multiple interface surfaces 506 configured to interface with a sealant, which in turn interfaces with the enclosure 202 to provide a water-tight seal (e.g., an IPX7-rated seal) to prevent ingress of moisture or debris. Each of the interface surfaces 506 faces away from the center axis 502 and toward the enclosure 202. Further, the interface surfaces 506 are (along the z-axis) between the flange 406 and the outer surface 310 of the lens 308.

Figure 6:
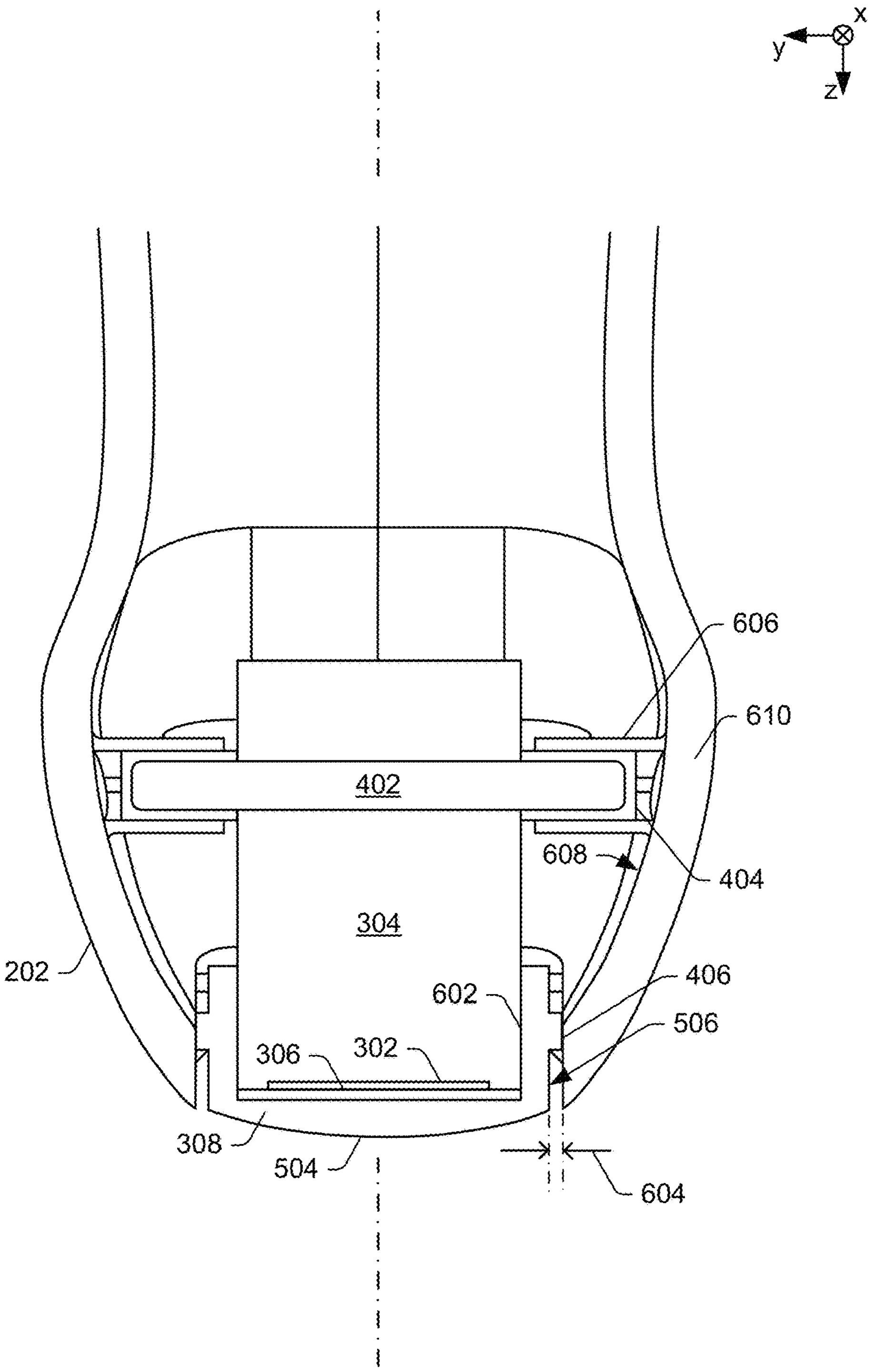
FIG. 6 illustrates a cross-sectional view of the ultrasound scanner from FIG. 2, taken along line A-A in FIG. 4.

FIG. 6 illustrates a cross-sectional view 600 of the ultrasound scanner 104 from FIG. 2, taken along line A-A in FIG. 4. In the illustrated example, the lens 308 forms a cavity for receiving at least the matching layers 306, the piezoelectric material 302, and a portion of the backing material 304. For example, the lens 308 includes sidewalls 602 extending from edges of the acoustic window 504 of the lens 308 to form the cavity wherein the matching layers 306, the piezoelectric material 302, and the portion of the backing material 304 are disposed. In this way, the lens 308 provides some structural support on the lateral sides (e.g., in the x- and y-directions) of the piezoelectric material 302 as well as on the front side (e.g., in the z-direction). As illustrated, the flange 406 interfaces with the enclosure 202. Also, the interface surfaces 506 of the lens 308 and the enclosure 202 are positioned distal to one another by a predefined distance or gap 604 sufficient to receive a sealant that seals the gap 604 against ingress of moisture or debris.

Also illustrated in FIG. 6 is the elongated member 402. The elongated member 402 is partially embedded within the backing material 304 and extends outwardly from opposing sides of the backing material 304 into corresponding holes in the enclosure 202. The holes in the enclosure 202 can be formed in any suitable way, including by an extending member 606 extending inwardly toward the central axis 208 from an interior surface 608 of the enclosure 202. In some implementations, an outer wall 610 of the enclosure 202 can have a width that is sufficiently thick to include or define the holes in the outer wall 610 itself. Between the hole(s) and the elongated member(s) 402 is the elastic material 404 (e.g., bushing), which dampens mechanical forces (e.g., impact forces) transferring from the enclosure 202 to the backing material 304.

Figure 7:
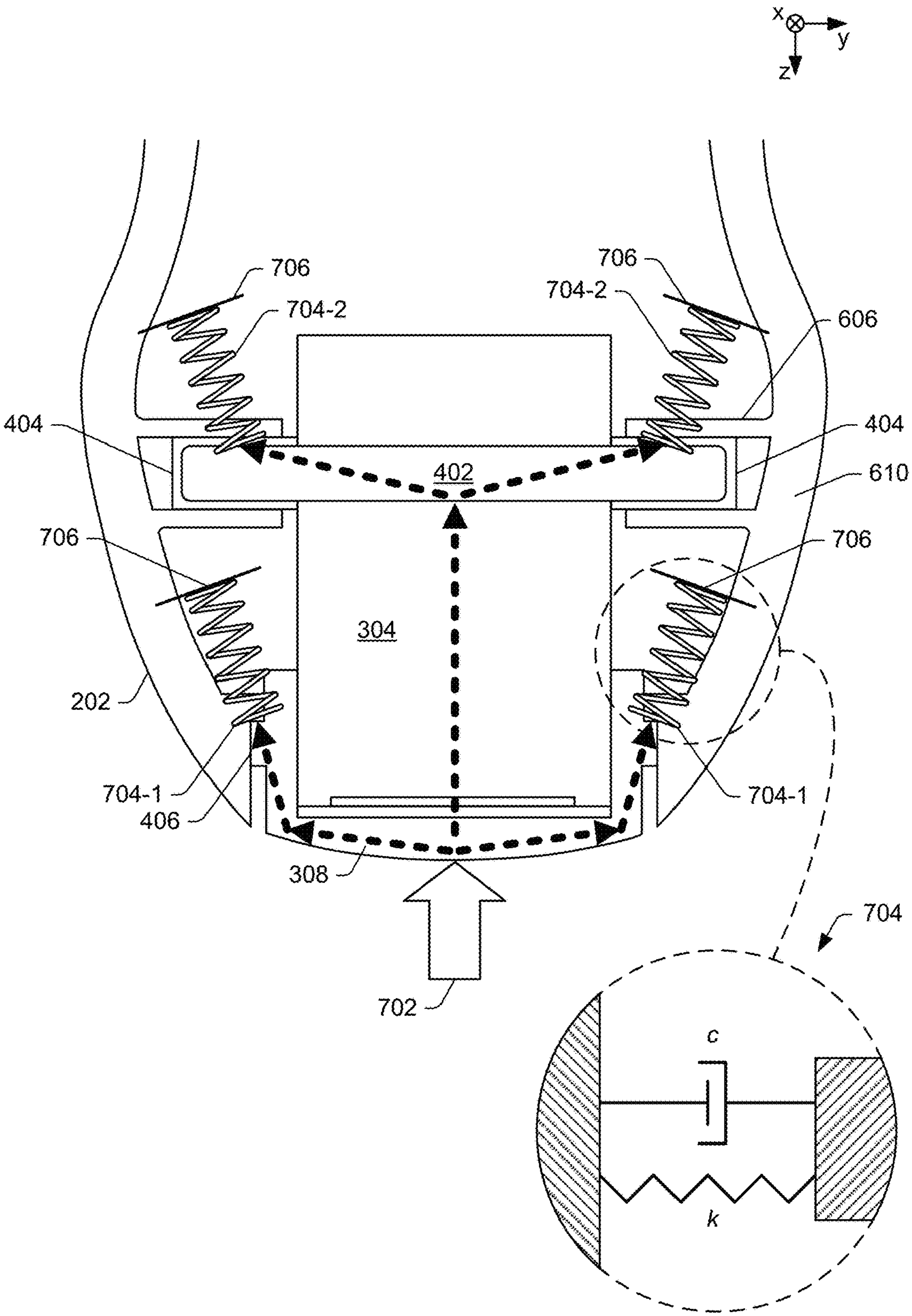
FIG. 7 illustrates an abstract example schematic of the impact-resistance system of the ultrasound scanner from FIG. 1 and an associated force distribution.

FIG. 7 illustrates an abstract example schematic 700 of the impact-resistance system of the ultrasound scanner from FIG. 1 and an associated force distribution. When an impact force 702 is applied directly to the lens 308 (e.g., the ultrasound scanner 104 is dropped directly on the lens 308), a portion (including a majority) of the impact force 702 passes through the lens 308 to the enclosure 202 via the lens-housing interface between the flange 406 and the enclosure 202. In some implementations, a layer of silicone or other suitable elastic material is disposed between the flange 406 and the enclosure 202 to ensure that no gap exists at the lens-housing interface. The ultrasound scanner 104 includes a plurality of spring-and-dampers 704 disposed in various locations to reduce peak acceleration of an impact force such as the impact force 702 and reduce oscillations associated with the impact force. The spring-and-dampers 704 are represented in FIG. 7 as interconnecting two nodes or masses and having both a spring constant k and a damping coefficient c. The spring-and-dampers 704 can be implemented in various ways. For example, the lens-housing interface acts as a first spring-and-damper 704-1 and is located between the flange 406 and a housing wall 706 (e.g., outer wall 610 or other wall) of the enclosure 202. The structure of the lens 308 diverts a portion (including the majority) of the impact force 702 around the piezoelectric material 302 and into the enclosure 202 via the sidewalls 602 and the flange 406.

A second spring-and-damper 704-2 is provided by the elastic material 404 (e.g., elastic bushing) disposed between the elongated member 402 and the housing wall 706 of the enclosure 202. This second spring-and-damper 704-2 reduces (e.g., by damping) peak acceleration associated with at least a portion of the impact force 702 passing through the backing material 304 to the elongated member 402 and then to the housing wall 706 via the elastic material 404. The second spring-and-damper 704-2 also reduces peak acceleration associated with at least a portion of an impact force passing from the enclosure 202 to the elongated member(s) 402 (e.g., from a side impact or from a returning wave of the impact force 702). An alternative implementation of the second spring-and-damper 704-2 can include a mechanical spring and/or a mechanical damper disposed between the elongated member 402 and the housing wall 706 of the enclosure. For example, a spring can be disposed between a first elongated member and the housing wall 706, and a damper can be disposed between a second elongated member and the housing wall 706, such that together the spring and the damper provide a system that reduces displacement caused by an impact force 702 to the enclosure 202.

Figure 8:
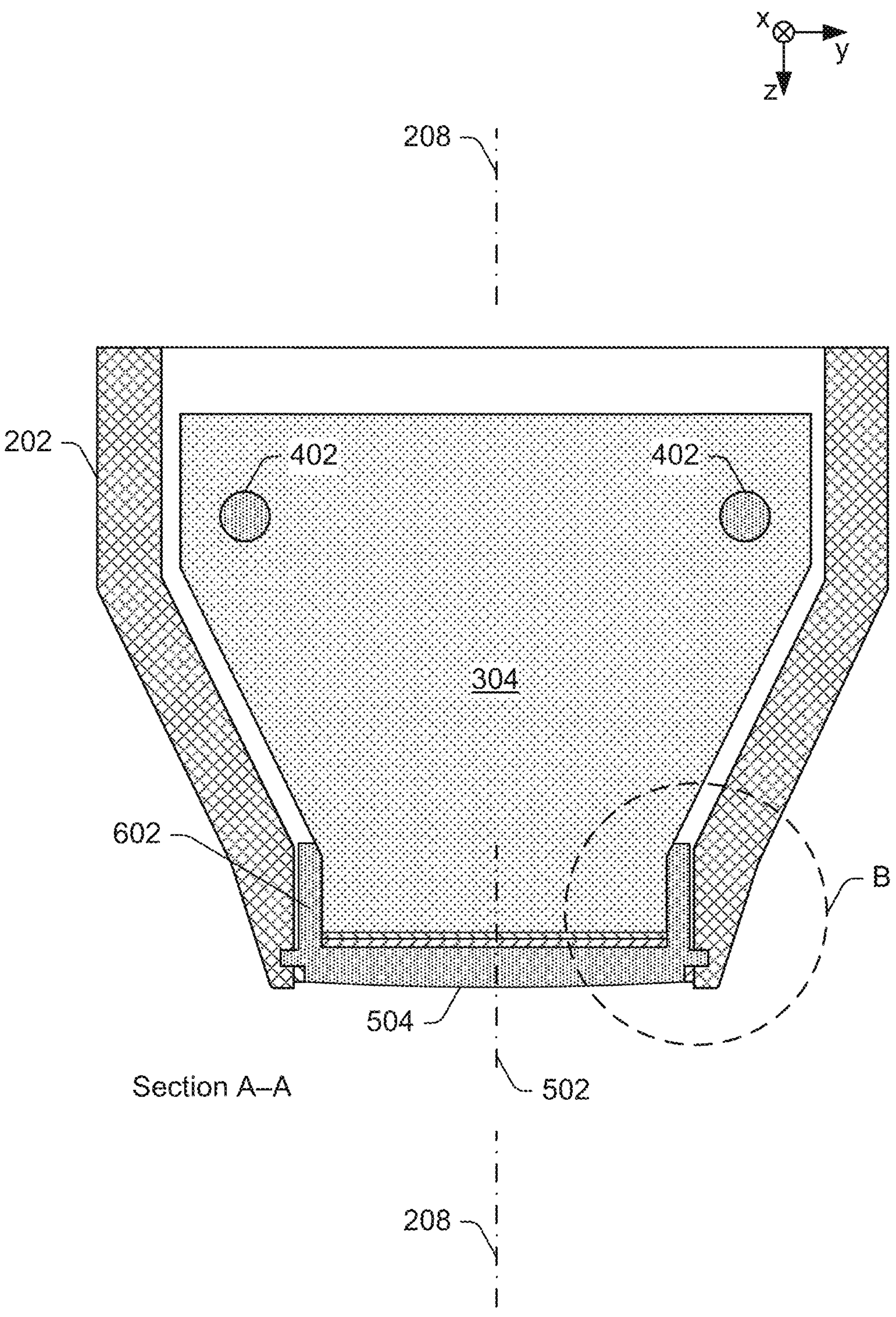
FIG. 8 illustrates a cross-sectional view of the portion of the example ultrasound scanner from FIG. 4, taken from line A-A in FIG. 4.

FIG. 8 illustrates a cross-sectional view 800 of the portion of the example ultrasound scanner 104 from FIG. 4, taken from line A-A in FIG. 4. As illustrated, the elongated members 402 are embedded in the backing material 304. Further, the structure of the lens 308 is such that the lens 308 includes sidewalls (e.g., sidewalls 602) that are connected to the edges of the acoustic window 504 and extend inwardly toward an interior of the enclosure 202 in a direction substantially parallel to the center axis 502 of the lens 308, which may be coaxial with the central axis 208 of the enclosure 202. A portion "B" of FIG. 8 is enlarged and shown in FIG. 9.

Figure 9:
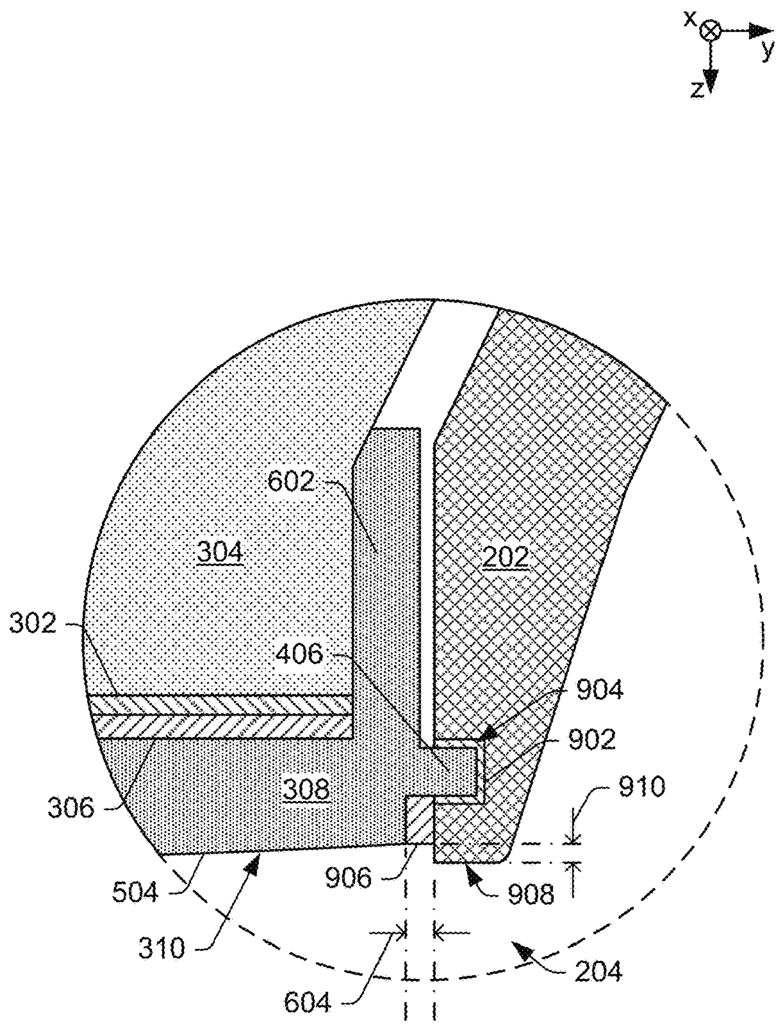
FIG. 9 illustrates an enlarged portion "B" taken from FIG. 8, showing a section of a distal end portion of the ultrasound scanner.

FIG. 9 illustrates an enlarged portion "B" 900 taken from FIG. 8, showing a section of the distal end portion 204 of the ultrasound scanner 104. In FIG. 9 is an example flange-and-channel interaction, as described above. For instance, the flange 406 can be disposed on one or more of the sidewalls 602 of the lens 308. The flange 406 extends laterally (e.g., non-parallel to, and outward from, the center axis 502 (from FIG. 8) of the lens 308) from the sidewalls 602 of the lens 308. The enclosure 202 includes a channel 902 (e.g., groove, recess, indentation, slot, etc.) that locates or receives the flange 406. In aspects, the channel 902 has a shape that substantially matches a shape of the flange 406.

During assembly of the ultrasound scanner 104, the flange 406 is directly captured by the channel 902 in the enclosure 202. In addition, at least one of the dimensions of the channel 902, including width, height, and depth, is greater than the corresponding dimension of the flange 406 to enable the channel 902 to receive the flange 406. This difference in dimensions creates a space or gap 904 between the flange 406 and the channel 902. The gap 904 is filled with an additional elastic material (e.g., silicone) to seal the gap 904 and to ensure that the flange 406 interfaces with the enclosure 202 (e.g., via the walls of the gap 904 in the channel 902). In addition, the gap 604 between the acoustic window 504 and the enclosure 202 is filled with a sealant 906 to seal the gap 604 against ingress of moisture and/or debris.

In some implementations, the impact-resistance system can also include a recessed lens (or a protruding portion of the enclosure). For example, the outer surface 310 of the acoustic window 504 can be recessed (e.g., inset) relative to an exterior surface 908 of the enclosure 202 at the distal end portion 204 of the ultrasound scanner 104. The lens 308 can be recessed by any suitable distance 910 in a range of, for example, one mil (0.001 inch, 0.0254 millimeter) to ten mil (e.g., 3.5 mil, 5.0 mil, 7.0 mil, etc.), including a range of three mil to six mil. By insetting the lens 308 from the enclosure 202 at the distal end portion 204 of the ultrasound scanner 104, a collision with a flat surface results in a majority of the impact force passing through the enclosure 202 rather than the lens 308 itself, thereby reducing how much of the impact force is applied to the piezoelectric material 302 in the transducer array.

Figure 10:
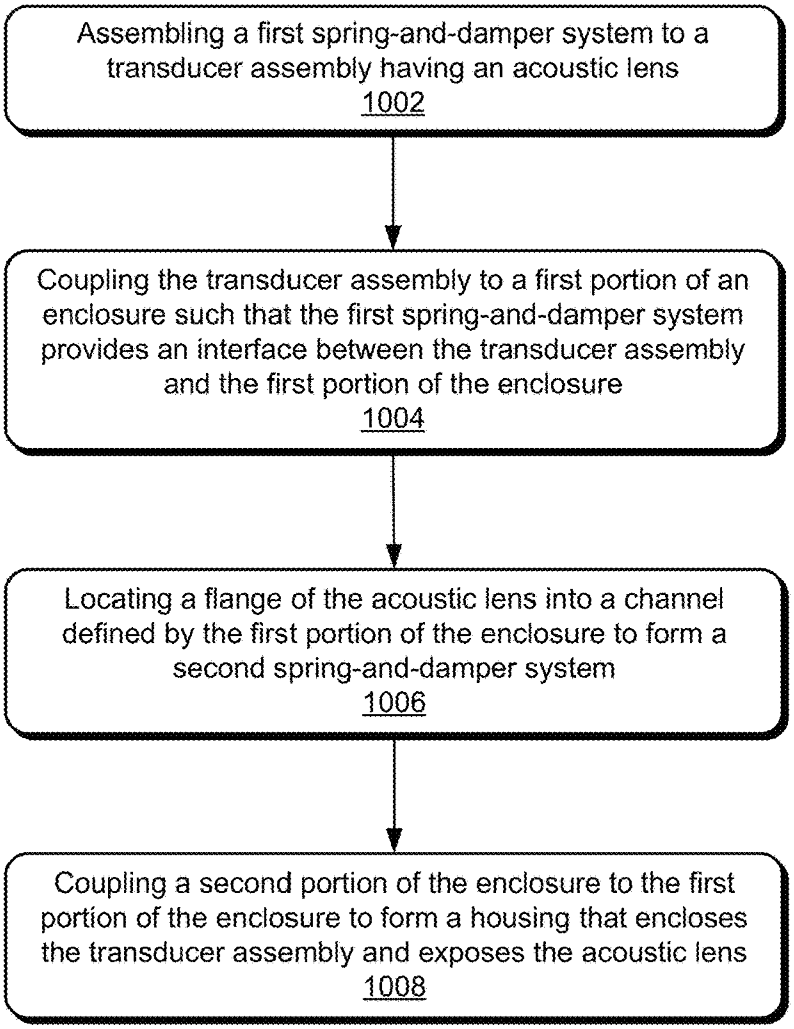
FIG. 10 depicts a method of assembly of an ultrasound scanner in accordance with one or more implementations.

FIG. 10 depicts a method 1000 of assembly of an ultrasound scanner in accordance with one or more implementations. The method 1000 is shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference may be made to the example system 100 of FIG. 1 or to entities or processes as detailed in FIGS. 2-9, reference to which is made for example only. The techniques are not limited to performance by one entity or multiple entities operating on one device.

At 1002, a first spring-and-damper system is assembled to a transducer assembly having an acoustic lens. For example, the first spring-and-damper system can include the elastic material(s) 404. In aspects, the first spring-and-damper system is coupled (e.g., press-fit, adhered, slidably mounted) to the elongated member(s) 402 that are embedded in the backing material 304 of the transducer assembly 214. In aspects, the elongated member 402 is inserted through an aperture in the spring-and-damper system. Alternatively, the first spring-and-damper system can be coupled to the first portion of the enclosure 202 (e.g., the elastic material 404 can be inserted into a hole in the enclosure 202 that is configured to receive the elongated member 402 of the transducer assembly 214).

At 1004, the transducer assembly 214 is coupled to a first portion of the enclosure 202 such that the first spring-and-damper system provides an interface between the transducer assembly 214 and the first portion of the enclosure 202. For example, the elongated member(s) 402 of the transducer assembly 214 is/are inserted into hole(s) in the first portion of the enclosure 202 such that the first spring-and-damper system is disposed between the elongated member(s) 402 and the enclosure 202.

At 1006, a flange of the acoustic lens is located into a channel defined by the first portion of the enclosure. For example, the acoustic lens 308 includes a flange extending from the acoustic lens 308 in an outward direction away from a center axis of the acoustic lens 308.

CONCLUSION

Embodiments of an ultrasound scanner with an impact-resistance system as disclosed herein are advantageous, as they can reduce effects of acceleration on the transducer caused by an impact force to the enclosure or to the lens area of the ultrasound scanner. The impact-resistance system disclosed herein provides a more robust and reliable ultrasound scanner, resulting in reduction of possible on-field damage from dropping the scanner on the floor or rough handling in clinical environments.

What is claimed is:

1. An ultrasound scanner comprising:

an enclosure extending between a first end and a second end;

a transducer assembly disposed at the first end of the enclosure and coupled to system electronics of an ultrasound machine, the transducer assembly configured to transmit ultrasound energy from one or more transducer elements toward a subject and receive ultrasound echoes from the subject for conversion by the one or more transducer elements into electrical signals usable by the system electronics to generate an ultrasound image, the transducer assembly including:

a backing material disposed within the enclosure;

a piezoelectric material disposed adjacent to the backing material; and an acoustic lens stacked with the piezoelectric material such that the piezoelectric material is between the acoustic lens and the backing material, the acoustic lens including:

an acoustic window configured to interface with the subject;

a center axis that intersects the acoustic window, the piezoelectric material, and the backing material; and sidewalls connected to the acoustic window and extending inwardly toward an interior of the enclosure in a direction substantially parallel to the center axis of the acoustic lens; and an impact-resistance system comprising a flange extending from the sidewalls of the acoustic lens in an outward direction away from the center axis of the acoustic lens and into a channel defined by the enclosure.

2. The ultrasound scanner of claim 1, wherein the flange is configured to interface with the enclosure via an elastic material disposed between the flange and the enclosure.

3. The ultrasound scanner of claim 1, wherein the impact-resistance system provides a spring-and-damper configured to reduce peak acceleration associated with an impact force applied to the enclosure.

4. The ultrasound scanner of claim 3, wherein the impact-resistance system provides the spring-and-damper configured to reduce a peak acceleration of the impact force that is non-orthogonal to the center axis of the acoustic lens.

5. The ultrasound scanner of claim 1, wherein the impact-resistance system provides a spring-and-damper configured to reduce peak acceleration associated with an impact force applied directly to the acoustic window of the acoustic lens.

6. The ultrasound scanner of claim 1, wherein:

the transducer assembly further includes one or more elongated members embedded in the backing material;

each of the one or more elongated members extends outwardly from opposing sides of the backing material and into a corresponding hole in the enclosure; and the impact-resistance system further comprises an elastic material disposed between the one or more elongated members and the enclosure.

7. The ultrasound scanner of claim 6, wherein the elastic material is an elastic bushing, an O-ring, a silicon rubber, a sealant, or an adhesive.

8. The ultrasound scanner of claim 6, wherein the elastic material is used as an interfacing bushing for attenuating an impact force applied to the enclosure or to the acoustic lens.

9. The ultrasound scanner of claim 1, wherein the acoustic lens is a recessed lens that is recessed from an exterior surface of the enclosure at the first end of the enclosure by a predefined distance.

10. The ultrasound scanner of claim 9, wherein the predefined distance of the recessed lens is in a range of three mil to six mil.

11. The ultrasound scanner of claim 10, wherein the predefined distance of the recessed lens relative to the exterior surface of the enclosure at the first end of the enclosure is approximately five mil.

12. The ultrasound scanner of claim 9, further comprising a sealant disposed between the acoustic lens and the enclosure and between the flange and an outer surface of the acoustic window.

13. The ultrasound scanner of claim 1, wherein the flange is disposed on two or more of the sidewalls of the acoustic lens.

14. The ultrasound scanner of claim 1, further comprising at least one matching layer, the at least one matching layer stacked with the piezoelectric material such that the piezoelectric material is between the backing material and the at least one matching layer.

* * * * *